United States Patent [19]

Stansbury

[11] 4,115,873
[45] Sep. 26, 1978

[54] HIGHLY STRETCHABLE GLOVE AND METHOD OF SIZING SAME

[75] Inventor: Benjamin Stansbury, Beverly Hills, Calif.

[73] Assignee: American Hospital Supply Corporation, Evanston, Ill.

[21] Appl. No.: 846,928

[22] Filed: Oct. 31, 1977

[51] Int. Cl.² .............................................. A41D 19/00
[52] U.S. Cl. ........................................... 2/163; 2/169
[58] Field of Search ................ 33/174 D, 178 R, 2 A, 33/2 R, 178 B; 2/163, 168, 169

[56] References Cited
U.S. PATENT DOCUMENTS
2,605,548  8/1952   Clarke ..................................... 33/2 R FOREIGN PATENT DOCUMENTS
288,221  10/1915  Fed. Rep. of Germany ............ 33/2 R Primary Examiner—Dorsey Newton
Attorney, Agent, or Firm—Larry N. Barger

[57] ABSTRACT

A series of latex rubber gloves for medical use in which a limited number of sizes comfortably fit a major portion of the general population. The glove sizes are positioned against the hand size distribution of the general population so the glove sizes are spaced further apart relative to palm circumference, and are spaced closer together relative to hand length. The gloves of this series have a comfortable stretch range of between 4 and 20% at palm circumference, and a comfortable stretch range of 1.5 to 10% relative to hand length.

15 Claims, 8 Drawing Figures

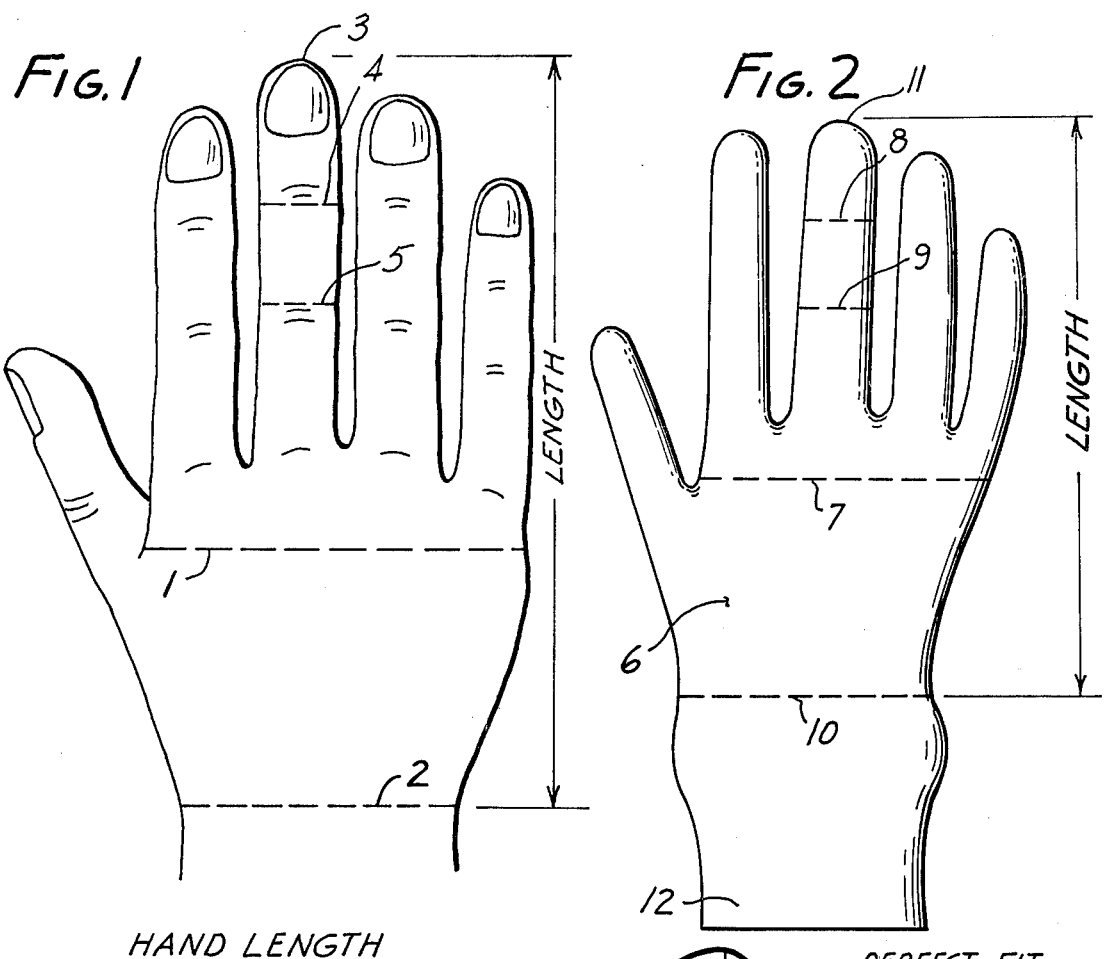
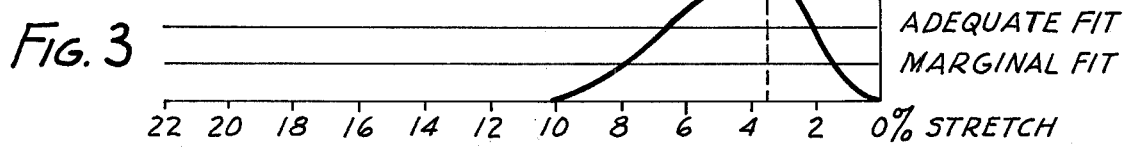
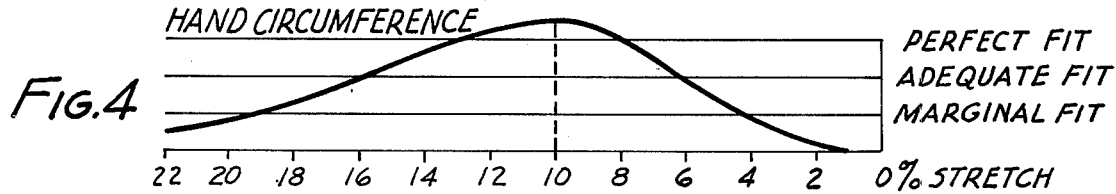
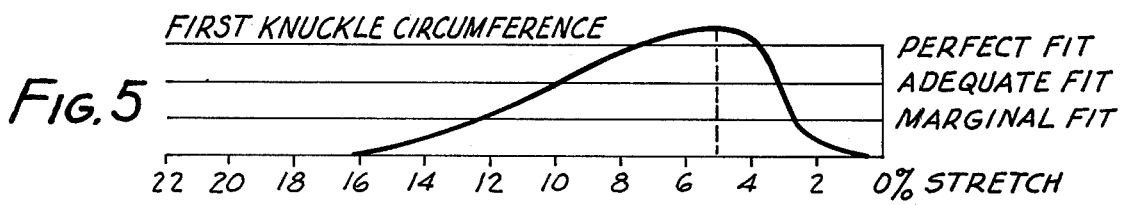
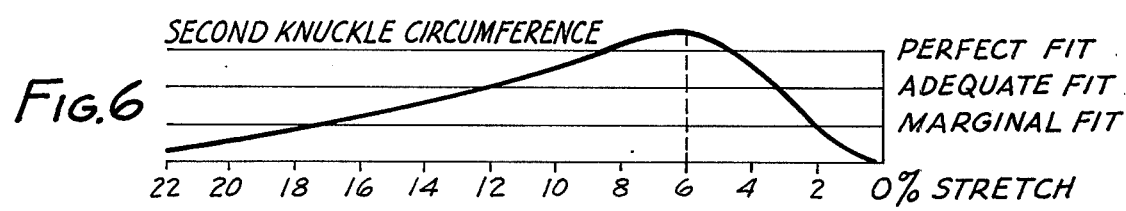

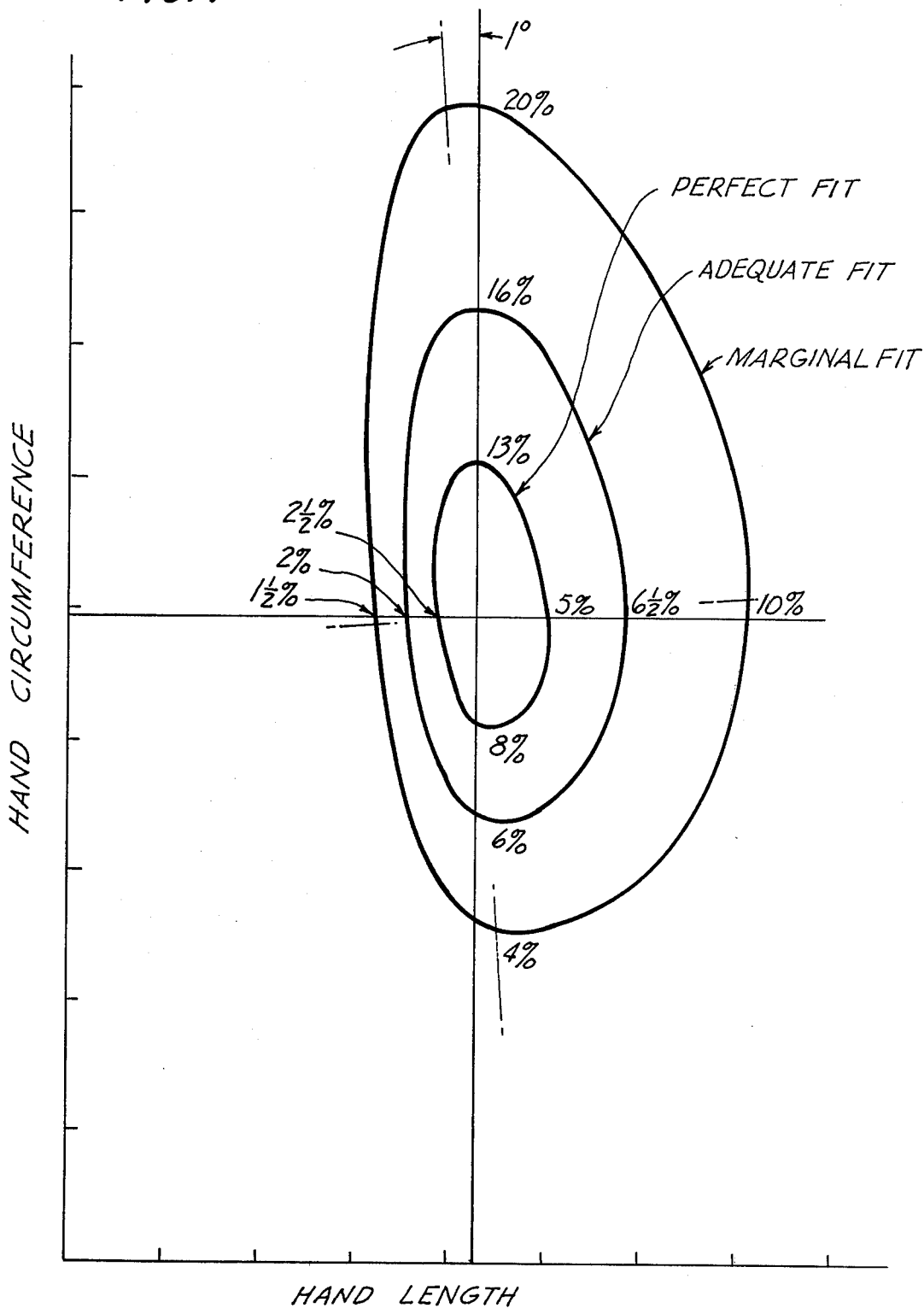

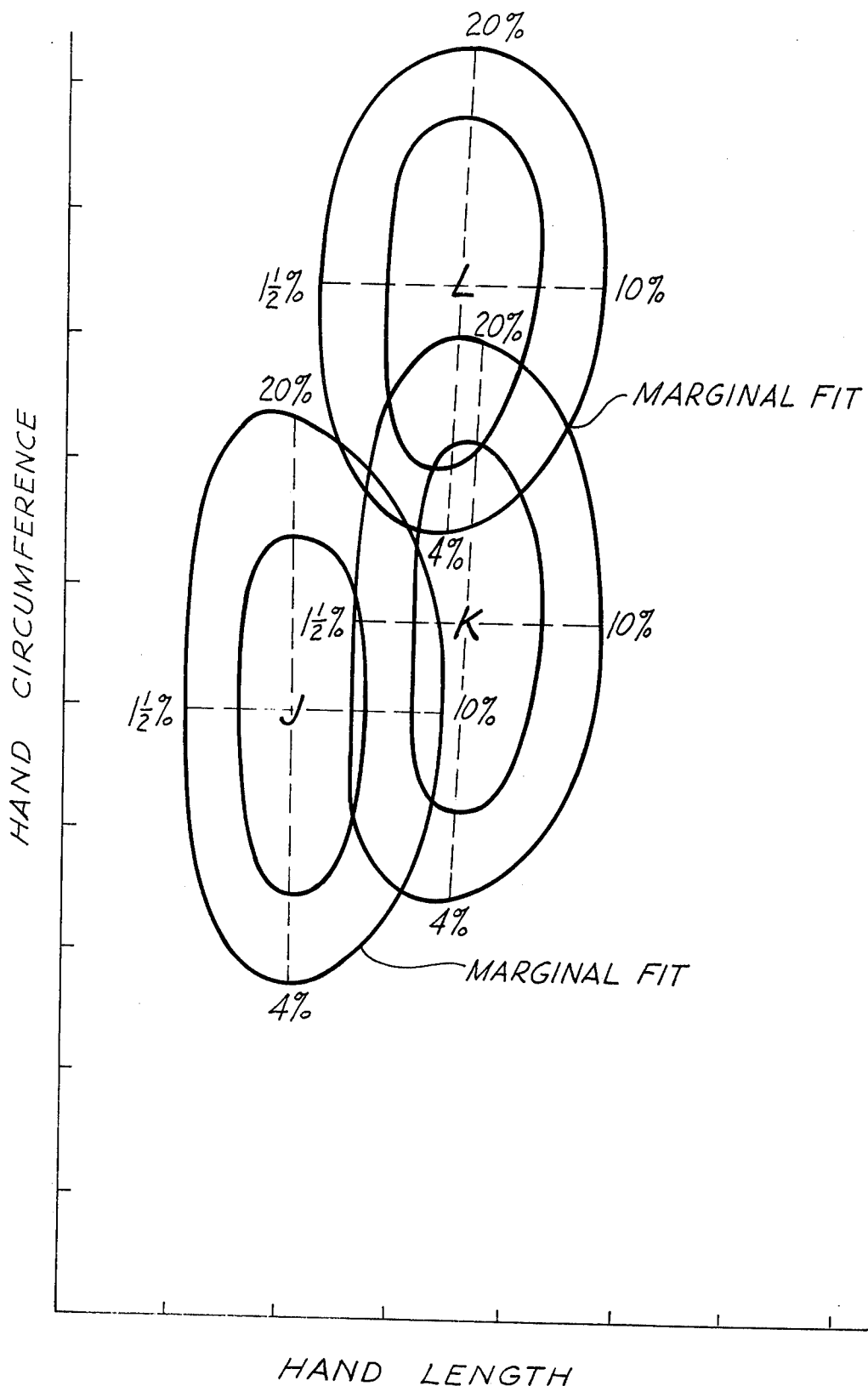

HIGHLY STRETCHABLE GLOVE AND METHOD OF SIZING SAME

BACKGROUND OF THE INVENTION

Latex rubber gloves are well-known for use by surgeons and other hospital and medical personnel. Because the latex rubber gloves are highly stretchable, a single glove size can be donned by different persons having substantially varying hand size and shape. In the past, latex rubber gloves in the medical field have been supplied in standard sizes such as 6½, 7, 7½, 8, etc. It is believed these historical sizes developed originally as having a very rough correlation to the circumference of a palm area of the user's hand. The glove length was made proportional to the circumference.

Because of the widely varying shapes and sizes of hands in the general population, a large portion of doctors, nurses, etc. could not get a comfortable fit from a latex rubber glove. This was partly due to areas of the glove being overstretched causing a fit that is too tight, or areas being understretched causing a baggy portion of the glove. Users often found that when a glove fit properly in the circumferential palm area, the glove's hand length, particularly in the finger area, was either too long or too short.

A large number of these latex rubber gloves are sold in a prepackaged sterile condition, and are discarded after a single use. This makes it uneconomical for a surgeon to have a latex rubber glove custom made for his particular hand size and configuration. Some people have very wide hands with short fingers, and conversely others have narrow hands with long fingers. Unlike shoe sizes, disposable surgeon's gloves cannot be economically produced and inventoried in various combinations of width and length. To do so would result in an estimated 50-60 different sizes.

SUMMARY OF THE INVENTION

To overcome the sizing problems with highly stretchable latex rubber gloves, this invention deals with positioning a limited number of sizes, 11 for instance, against the distribution of hand sizes in the general population, so that substantially all of this population can find a glove that will comfortably fit them both to length and to palm circumference (width). It has been unexpectedly found that there is a much larger tolerance for a stretch range (4 to 20%) in the palm circumference area than in the hand length area (1.5 to 10%). Within these stretch ranges, the glove feels comfortable to the user. Below this stretch range, a glove feels too loose, and above this stretch range a glove feels too tight.

The glove sizes of this invention have been positioned to provide overlapping comfortable fit ranges. Adjacent glove sizes are incrementally spaced further apart relative to percentage stretch at the glove palm circumference area, and spaced are incrementally closer together relative to percent at a hand portion of the glove.

THE DRAWINGS

FIG. 1 is a plan view of a typical user's hand, showing the positions at which measurements are taken;

FIG. 2 is a plan view of a latex rubber glove in its unstretched condition;

FIG. 3 is a graph showing how a comfortable fit relates to percentage of stretch in a hand length portion of the glove;

FIG. 4 is a graph showing how a comfortable fit relates to percentage stretch at a palm circumference of the glove;

FIG. 5 shows a graph of how a comfortable fit relates to percentage stretch at a first knuckle circumference of the glove;

FIG. 6 is a graph showing how a comfortable fit of the glove relates to a percentage stretch at a second knuckle circumference of a glove finger;

FIG. 7 is a plot of the curve shown in FIG. 3 versus the curve shown in FIG. 4; and FIG. 8 is a graph showing the positioning of three glove sizes illustrating how their comfortable fit stretch characteristics overlap.

DETAILED DESCRIPTION

FIG. 1 shows a user's hand in which a palm circumference is measured at a location indicated at 1 and a hand length taken from a wrist area to tip of index finger 3. A first knuckle circumference is measured at 4 and a second knuckle circumference is measured at 5.

FIG. 2 shows a highly stretchable latex rubber glove 6 in its unstretched condition prior to donning. The palm circumference is measured at 7 and the first and second knuckle circumferences measured at 8 and 9 of the glove. The length of a hand portion of the glove is measured from a wrist area 10 to a tip 11 of the glove's index finger portion. Because gloves can vary substantially in cuff length, thickness, and width, a cuff 12 of the glove is not included in calculating the length of the glove's hand portion. It is in the hand portion of the latex rubber glove where most of the ill fitting problems occur.

Unlike a leather or fabric glove, which is generally nonstretchable, a highly stretchable latex rubber surgeon's glove must be substantially undersized to provide a comfortable fit. The gloves can have a thickness of from 0.005 inch to 0.020 inch to provide tactile sensitivity. A latex rubber glove that has very little or no stretch after donning, provides the user with a glove that feels uncomfortably too large, even though the glove may precisely conform to the hand shape of the user.

FIG. 3 shows the percent stretch along the length of the glove's hand portion as this stretch relates to fit. At approximately 3.5 percent stretch the user has what is termed a "perfect fit" on the graph. This perfect fit can also extend in the range of approximately 3 to 5%. When the stretch goes beyond these figures and extends out to either 2% on the low stretch end or 6.5% on the high stretch end, the user still has an "adequate fit." Further extending the stretch limit to approximately 1.5% on the low end and 8% on the high end yields a "marginal fit," but a fit that is still considered comfortable to the user. Below 1.5% stretch the user has an uncomfortably loose glove, and above 8% stretch the user has an uncomfortably tight glove as relates to hand length.

FIG. 4 is a plot similar to FIG. 3, but relating percent stretch at a circumference of a palm area of the glove to its fit. It is noted that fit tolerance in the hand or palm circumference area is substantially greater as a percent of stretch than is the hand length shown in FIG. 3. In FIG. 4 a marginal, but comfortable, fit can extend between 4 and 20% stretch. Below 4% stretch the glove feels uncomfortably loose in the palm area. Above 20% the glove is circumferentially squeezing the palm to such an extent that the glove is uncomfortable.

FIGS. 5 and 6 are plots of the percent stretch versus the glove fit at the first and knuckle circumferences. It is noted that the knuckle areas have a substantially greater tolerance in the stretch area than does the glove in the hand length area.

The two most critical areas of the glove are hand length and hand circumference. These two variables have been plotted against each other in the FIG. 7 plot. This plot resembles an oval configuration that was slightly flattened on one side and had its major and minor axes offset approximately 1° from the graft's horizontal and vertical axes.

In FIG. 7, the numerical coordinance have been left off of the left and bottom section of the graph, but they have been indicated on the oval plots on the graph. For instance, the "perfect fit" area indicates hand length can vary from 2½ to 5% stretch. Hand circumference can go from 8 to 13% in a perfect fit situation.

Since it is desirable from an economical standpoint to have as few glove sizes to provide a comfortable fit to the majority of the population, the marginal, but comfortable, glove is of most concern. As shown in FIG. 7, the hand length can carry from to 1½ to 10% stretch and still fit the wearer comfortably. The hand circumference can vary within the range of 4 to 20% stretch and still be comfortable.

FIG. 8 shows the incremental positioning of three glove sizes to provide overlapping comfortable percentage stretch in both the hand length and hand circumference areas. Since the gloves no longer bear a relationship to the traditional sizes 6½, 7, 7½, 8, etc., a new size indicating system is preferable. Here the letters of J, K, and L have been used, but other sizing designations can be used, if desired. If a surgeon trys on a size J glove and finds that the palm circumference stretch lies on the dotted horizontal line through glove J, he is getting an "adequate" fit and perhaps even a "perfect" fit. In FIG. 8 the small center oval indicating the perfect fit has not been shown. If this physician has a very long hand, he may require a 10% longitudinal stretch of the hand portion of the glove placing his fit in a right hand margin of the marginal, but comfortable, fit of the J glove. In this situation, he would be better off with a size K glove because his hand would now be fitting in the "adequate" fit area that lies between the "perfect" fit and "marginal," but comfortable, fit.

As seen in FIG. 8, the glove sizes are positioned to overlap in the comfortable (marginal) fit areas. Because of the greater tolerance in the percent stretch in the palm circumference area than in the hand length area, the sizes of the gloves are positioned manipulated into positions relative to each other as shown in FIG. 8. Here glove J and K are very close to each other relative to hand length (horizontal direction in FIG. 8). Glove sizes L and K are substantially further apart (vertical direction in FIG. 8) to reflect the greater tolerance in percent stretch at the palm area. While only three glove sizes have been used to illustrate this invention, these glove sizes can be of any number, such as from 5 to 20 different sizes. A good representative number of sizes would be 10–12. Thus, substantially all of the nurses and physicians could readily find a glove size that would comfortably fit them whether their fingers are long or short, or their hands are wide or narrow in the palm area. For instance, in FIG. 8 glove size L is located almost directly above glove size K. This indicates that both gloves L and K have approximately the same length in the hand area. However, glove L is a substantially wider glove (palm circumference shown vertical on FIG. 8).

The present invention has to do with a series of gloves and their particular sizing relationship and the method of positioning the sizes against the population distribution of hand sizes. The individual glove of this series is described in my co-pending application entitled Glove and Form For Making Same, Ser. No. 846,911, filed Oct. 31, 1977. A co-pending application entitled Hand Measuring Device and Method of Selecting Glove Sizes, Ser. No. 846,924, filed Oct. 31, 1977 describes a device with which a physician can measure his hand and immediately determine whether he needs a size J, K, or L glove.

In the foregoing description specific examples have been used to describe this invention. However, those skilled in the art will understand that certain modifications can be made to these examples without departing from the spirit and scope of the invention.

I claim:

1. A series of highly stretchable gloves of different sizes, the series consisting of gloves with incremental differences in the lengths of the glove hand portion that are smaller than the incremental differences in the circumferences of the glove hand portion, whereby a reduced number of gloves are needed to properly fit a wide variety of hand shapes.

2. A series of gloves as set forth in claim 1, wherein the gloves in the series have a percentage stretch range for a comfortable fit at a circumference of the glove's hand portion that is approximately twice the percentage stretch range at the length of the glove's hand portion.

3. A series of gloves as set forth in claim 2, wherein the gloves in the series have a comfortable fit in the hand circumference over a stretch range of approximately 16% between its upper and lower limits.

4. A series of gloves as set forth in claim 3, wherein the gloves in the series have a comfortable fit when the circumference of the glove's hand area is stretched at least 4%, but not more than 20%.

5. A series of gloves as set forth in claim 2, wherein the gloves in the series have a comfortable fit over a stretch range of the glove's hand length of approximately 8.5% between its upper and lower limits.

6. A series of gloves as set forth in claim 5, wherein the gloves in the series have a comfortable fit when the glove's hand portion is stretched along its length at least 1.5%, but not more than 10%.

7. A series of gloves as set forth in claim 1, wherein the series has from 5 to 20 different glove sizes.

8. A series of gloves as set forth in claim 1, wherein the gloves in the series are of a latex rubber material having a thickness of from 0.005 inch to 0.020 inch in the glove's hand area when the gloves are in an unstretched condition.

9. A series of gloves as set forth in claim 1, wherein two adjacent glove sizes have overlapping comfortable fit ranges at a circumference of the glove's hand area; and said adjacent glove sizes can reach a common hand circumference by the larger of the two stretching 4% or more and the smaller of the two glove sizes stretching 20% or less at the circumferences of hand portions of the two gloves.

10. A series of gloves as set forth in claim 1, wherein two adjacent glove sizes have positions with overlapping comfortable fit ranges relative to lengths of the hand portions of the two gloves; and said adjacent glove sizes can reach a common hand length by the larger of the two glove sizes stretching 1.5% or more and the smaller of the two glove sizes stretching 10% or less.

11. A series of highly stretchable gloves of between 5 and 20 different sizes, the series consisting of gloves with incremental differences in the lengths of the glove hand portion that are smaller than the incremental differences in the circumferences of the glove hand portion; said series having at least two adjacent glove sizes that reach a common glove hand circumference by the larger glove stretching 4% or more and the smaller glove stretching 20% or less in the glove hand circumference; and the series has at least two adjacent glove sizes that reach a common glove hand length by the larger glove stretching 1.5% or more and the smaller glove stretching 10% or less in the glove hand length.

12. A method of sizing highly stretchable gloves to fit a wide variety of hand shapes comprising the steps of: selecting a limited number of sizes; and manipulating these sizes into positions so that incremental differences in the lengths of the glove hand portion are smaller than the incremental differences in the circumferences of the glove hand portion.

13. A method as set forth in claim 12, wherein the limited number of sizes selected are in the range of 5 to 20 different glove sizes.

14. A method as set forth in claim 12, wherein the method includes positioning two adjacent glove sizes so that these adjacent glove sizes can reach a common hand circumference by the larger of the two gloves stretching 4% or more and the smaller of the two gloves stretching 20% or less in the glove hand circumference.

15. A method as set forth in claim 12, wherein the method includes positioning two adjacent glove sizes so that said adjacent glove sizes can reach a common glove hand length by the larger of the two gloves stretching 1.5% or more and the smaller of the two gloves stretching 10% or less in the glove hand length.

* * * * *